United States Patent [19]

Wang

[11] Patent Number: 4,643,179

[45] Date of Patent: Feb. 17, 1987

[54] WOUND COVERINGS AND PROCESSES FOR THEIR PREPARATION

[76] Inventor: Paul Y. Wang, 47 Marblemount Crescent, Agincourt, Ontario, M1T 2H5, Canada

[21] Appl. No.: 247,604

[22] Filed: Mar. 25, 1981

[51] Int. Cl.$^4$ .......................... A61F 13/00; A61F 5/44
[52] U.S. Cl. ..................................... 128/156; 128/155
[58] Field of Search ............... 128/155, 156, 260, 268, 128/283; 3/1; 424/32, 35

[56] References Cited

U.S. PATENT DOCUMENTS

| | | | |
|---|---|---|---|
| 3,339,546 | 9/1967 | Chen | 128/283 |
| 3,712,304 | 1/1973 | Marsan | 128/283 |
| 3,799,166 | 3/1974 | Marsan | 128/283 |
| 4,192,785 | 3/1980 | Chen et al. | 128/283 |
| 4,253,460 | 3/1981 | Chen et al. | 128/283 |
| 4,310,509 | 1/1982 | Berglund et al. | 128/268 |

*Primary Examiner*—John F. Terapane
*Assistant Examiner*—T. J. Wallen
*Attorney, Agent, or Firm*—Lawrence Rosen

[57] ABSTRACT

Skin covering materials especially for wounds comprise dextran C insolubilized by reaction with epichlorohydrin in combination with a suitable humectant. The compositions may be in the form of coherent, self-supporting sheets of the insolubilized dextran C impregnated with humectant material, or in the form of pastes applied to the wound as such. The humectant material is preferably glycerin or isopropanolpropylene glycol and an oil. The wound covering material allows sufficient removal of exuded body fluid and seals the wound site against bacterial infection, whilst at the same time maintaining the wound moist to prevent scale formation. Medicaments may additionally be incorporated into the wound covering material, to assist in healing and further to safeguard against bacterial infection.

5 Claims, No Drawings

WOUND COVERINGS AND PROCESSES FOR THEIR PREPARATION

FIELD OF THE INVENTION

This invention relates to materials for use with living skin tissue, for protection thereof, and methods for their preparation and use. More particularly it relates to wound covering compositions and methods.

BACKGROUND OF THE INVENTION

Skin injuries have only recently been recognized as serious health problems. Damage to the protective, skin layer of a living body has conventionally been regarded as superficial, and not serious. However, such surface injury leads to loss of vital body fluid by evaporation, which can initiate a series of changes in body functions that are difficult to restore immediately. In addition, skin damage may permit the invasion of the underlying body tissues by harmful microorganisms. When body fluids evaporate from a skin damage site, e.g. a wound site, a layer of scale will form at the site, which delays the healing process and the formation of new tissue.

BRIEF REFERENCE TO THE PRIOR ART

For many years, textile materials have been applied as temporary coverings for wounds, to prevent evaporative loss, infection and to promote healing. Such materials tend to adhere tenaciously to the wound site. More recently, non-adherent perforated thermoplastic films have been used, with absorbent inner pads, as described for example in Canadian Pat. No. 798,094. Dressings of this type, however, do not seal at the edges to prevent bacterial ingress to the wound. It is also known to use polyurethane films (Op-Site) which can adhere to intact skin around a wound, to seal against bacterial ingress. Such films allow limited transmission of exudative fluid by evaporation through the film matrix, but do not absorb exudates immediately, which can be a very serious problem especially in infected wounds that drain profusely.

In an attempt to overcome these shortcomings, attempts have been made to utilize natural skin from other sources as temporary wound coverings. Thus, processed porcine skin and human cadaver skin have begun to gain popularity for this purpose. They have the disadvantages of expense, limited availability and the risk of inducement of undesirable immunological reactions in the recipient.

A satisfactory wound covering should be capable of substantially reducing evaporative losses of body fluids, whilst at the same time removing in some appropriate manner reasonable amounts of fluids from a wound site. In other words, the wound site should be kept moist in order to prevent scale formation, but free from excess exudates of body fluid to promote healing and reduce bacterial contamination risk. The wound covering should also seal the wound against secondary infection, be capable of conformation to uneven wound site surfaces and have the required biocompatiblilty. Ease of application and removal are other desirable characteristics.

SUMMARY OF THE INVENTION

It is an object of the present invention to provide a novel wound surface covering material.

It is a further object of the present invention to provide a wound covering which satisfies one or more of the above criteria.

The present invention provides a form of wound covering which utilizes as its principle components insolubilized dextran, preferably dextran C in combination with a humectant. In one embodiment, the dextran and humectant are formed into a coherent sheet or film, which is placed over the damaged skin area to cling to the wound site. In another embodiment, the dextran and humectant are formed into a paste, which is applied as such to the wound site.

Dextran C is natural polysaccharide material, widely used in various biological applications. Its biological and immunological properties are thus quite well known and well understood. Dextran C has a molecular weight of less than 100,000 daltons, and is widely accepted for use clinically as a plasma expander. Dextran varieties of molecular weight above about 100,000 daltons are antigenic, so that they cannot be tolerated by all patients although useful in some cases.

For use in the present invention, the dextran C is insolubilized. This is best accomplished by reacting the material with epichlorohydrin. There are many reactive difunctional or polyfunctional organic chemical compounds which will react with clinical dextran C to cause insolubilization thereof. Typical of such polyfunctional compounds are diacyl chlorides, dicarboxylic acid anhydrides, diisocyanates, dithioisocyanates, diimines, disulfonyl chlorides, dicarbonyls and diepoxides. Most preferred is epichlorohydrin, on account of its high reactivity with the dextran C in aqueous alkaline solution, and especially on account of the conversion of the unreacted epichlorohydrin under the insolubilization reaction conditions into the neutral and biologically compatible glycerin, a component of natural fats. Other possibly suitable reactants may not lead to the formation of biologically harmless by-products.

The wound coverings of the present invention incorporate a humectant, for the purpose of holding moisture etc. in the vicinity of the wound site. The dextran materials alone have only limited ability to hold moisture at the body temperature of about 37° C. Simple organic hydroxyl or polyhydroxyl compounds have the ability to absorb moisture from atmosphere and also when present as a component of a solution. They depress the vapour pressure of other polar liquids, thus reducing their evaporative tendencies by molecular association. Since the materials of the present invention are to be used on exposed internal tissues after surface skin damage, it is preferred to use USP grade glycerin, propylene glycol, isopropanol-propylene glycol mixtures or other suitable biocompatible combinations thereof. As discussed below, these specific humectant materials also have the advantage of compatibility with many antibacterial drugs employed to treat infected wounds. The humectant should also include an oil, to limit the absorbance of the covering material and hence the rate at which it will absorb exudates. The oil should of course be biocompatible. Suitable specific examples include mineral oils, castor oil and petrolatum.

For use in the present invention, the compositions may be preformed as sheets, or applied as semi-solid pastes. In preparing the materials, firstly, insolubilization of the dextran is conducted, and subsequently combination with the humectant is undertaken. For insolubilization, clinical dextran C may be dissolved in deionized double distilled water in a suitable vessel, and concentrated sodium hydroxide solution added, followed by addition of epichlorohydrin. A two phase liquid system is formed, which is immediately agitated by means of a suitable stirrer. Vigorous stirring is undertaken, to disperse immiscible epichlorohydrin to a fine dispersion in the alkaline dextran solution, but minimizing splashing. The vigorous stirring is continued for about seven minutes, to obtain a hazy dispersion. Excess mixing, beyond the formation of a clear lemon-yellow solution should be avoided.

In one embodiment of the invention, a continuous sheet or sheet of the material is formed. This can be accomplished by introducing the dispersion between polyethylene sheet layers, e.g. polyethylene sheets carried by glass plates, and clamping the sheets together to avoid leakage of the dispersion from between them. In 6–8 hours at room temperature (21° C.), the liquid mixture first turns into a clear lemon-yellow solution and then into a coherent continuous sheet which can easily be removed from the polyethylene sheet lining and transferred into a large bath with running hot water (60° C.) to remove residual alkali. The coherent continuous sheet of insolubilized dextran C so formed is observed to expand to about 50% of its original size, and then the running water is turned off and the water in the bath is removed by aspiration without disturbing the sheet. Then, the sheet is impregnated with humectant material. For this purpose, an excess amount of isopropanol in propylene glycol is then added to the bath, completely to cover the sheet. A suitable isopropanol concentration is 15% in the propylene glycol. In about 24–48 hours, the sheet shrinks by about 20% of its original size and becomes saturated with the alcohol-glycol mixture. At this point, the sheet can be folded, pressed or stretched, and will have an elongation at break of about 60–100%.

In a preferred embodiment of the invention, antimicrobial or other medicinal compounds may be incorporated into the wound covering material, to assist in the healing process. An example of a suitable such antimicrobial agent is polyvinylpyrrolidone-iodine complex. This is suitably accomplished by adding the antimicrobial material into the alcohol-glycol bath after the sheet has been washed with hot water.

The above described process produces sheets of thickness, for example, 0.1 cm, as arranged by the separation of the polyethylene sheets. If thicker sheets are required, the amount of deionized, double distilled water is increased and the separation of the polyethylene sheets is appropriately increased. This extra amount of water present during the insolubilization reaction has been found to result in a sheet with surfaces slightly tackier than that prepared as described above. This increased thickness allows the insolubilized dextran sheet to absorb larger volumes of fluid at the wound site, whilst the increased tackiness may be helpful in positioning the sheet over the wound site.

Sheets of thickness greater than about 0.1–0.2 cm are prepared with perforated, inert, water swellable polymer sheets such as cellophane embedded in the insolubilized dextran sheet to add dimensional stability. Woven textile materials may also be used but are less satisfactory. This may be accomplished by including the perforated polymer sheet or woven textile material in the space between the polyethylene plates between which the sheet of insolubilized dextran is to be formed. Subsequently, the sheet is impregnated with the humectant material and, if desired, the antimicrobial material (polyvinylpyrrolidone-iodine complex), as previously described.

In another embodiment of the invention, the wound covering is formed as a uniform paste, for application by hand to a wound site, or for preparation of a sheet for application, from the paste. For this purpose, the dextran is insolubilized as previously described, but a larger amount of deionized, double distilled water is used in the insolubilization process, approximately twice as much as used in the material from which sheet is to be prepared directly. Very large excesses of water should be avoided, or the insolubilization reaction may not proceed properly. The hazy dispersion produced after the vigorous stirring is left undisturbed for about 8–14 hours, whereupon a block of elastic insolubilized dextran C is formed. The block is broken up and transferred into a container with excess distilled water. The water is changed every 8 hours for 4 days, and the insolubilized lumps of dextran C are recovered by filtration, and homogenized in a high speed blender to give a smooth paste. The thin uniform paste is agitated continuously while being thickened by evaporation to yield a paste with 20–23% solid content of the insolubilized dextran by weight. Higher solid contents yield a paste which is difficult to spread. The paste is then mixed thoroughly with glycerin to achieve a final concentration of about 20% based on the final weight of the paste. Antimicrobial agents may be added separately to the glycerin before mixing the liquid mixture with the paste, if desired.

This paste can be used as such, or alternatively, an insolubilized dextran C sheet may be prepared therefrom. For this purpose, the smooth paste so prepared is spread evenly and then pressed between two polyethylene sheets. The thickness and size of the sheet can be controlled by guard strips of polyethylene slabs along the sheet edges. Again, as previously described, a perforated elastic sheet may be sandwiched between two sheets of insolubilized dextran C prepared from the paste, to add reinforcement.

The preferred concentration of humectant materials to be dispersed in the dextran sheets of greater than 0.1–0.2 cm thickness is from about 20% to about 50% by weight, based upon the weight of the insolubilized dextran C, and preferably from about 30% to about 50%. If the concentration of humectant is too low, too fast a drying rate may result, causing stiffness of the wound covering material of the invention. When the material is used in paste form, it is preferred not to exceed a value of 30% concentration for the humectant, otherwise there may result excessive cohesion of the insolubilized dextran material, rendering spreading of the paste on the wound site or on polyethylene sheets for pressing into sheets difficult.

Whilst a wide range of different antibacterial and the like medicaments can be incorporated into the coverings of the present invention, if desired, the preferred such antibacterial drugs are silver sulfadiazine and polyvinylpyrrolidone-iodine complex. These are broad spectrum drugs having wide range of activity against the many types of microorganisms found in infected skin wounds. Antibiotics such as penicillin and its derivatives are not generally effective as topical agents against such microorganisms. Moreover, the preferred antibacterial drugs have the necessary stability in the humectant present in the insolubilized dextran sheets and paste.

The invention is further described by the following specific examples, which are presented as illustrations, and not intended to limit the scope of the invention.

EXAMPLE 1

An amount of 15 g of clinical dextran having a molecular weight of about 60,000 daltons was dissolved in 60 ml of de-ionized double distilled water in a 250-ml beaker. A volume of 6 ml of a 10 N sodium hydroxide solution was added slowly with stirring into the dextran solution. Epichlorohydrin in an amount of 4.5 ml was measured by a graduated pipette and added into the alkaline dextran solution, followed by vigorous stirring as described above. The well-stirred and now hazy solution was drained as a fine stream into a polyethylene sheet lined vertical U-shaped tank compartment having a dimension of 16 cm by 16 cm and a thickness of 0.1 cm. After hours at room temperature, the compartment was dissembled and the thin insolubilized dextran sheet removed and placed in a tray with running hot water. When the sheet had expanded to about 40% of its original size, the water was turned off and syphoned carefully from the tray. A mixture of 15% isopropanol in propylene glycol containing 1% castor oil was then added to the tray to cover the dextran sheet completely. The isopropanolpropylene glycol solution was changed after 24 hours, and the dextran sheet was removed from the solution bath after another 24 hours. There was about 20% reduction in size of the sheet as compared to its original dimension after saturation with the organic humectant solution. Elongation measurement on a Chatillon motorized tensiometer showed an extension of 82% extension at break. Extraction of a piece of the thin insolubilized dextran sheet just prepared by 1,4-dioxane and analysis of the extract on a Beckman gas-liquid chromatograph showed no detectable epichlorohydrin, although control experiments demonstrated that trace amount, if present, of this reactive organic compound used in the insolubilization process could readily be detected.

TEST 1

Covering for Skin Abrasion in Vivo

Male Wistar rats weighing 400±20 g were divided into a group of 10 and another group of 15. In a typical procedure, the dorsal skin of an anaesthetized animal was shaved closely between the occiput and sacrum, followed by thorough scrubbing of the shaved area with a 10% aqueous solution of polyvinylpyrrolidone-iodine complex. An area 3 cm by 3 cm was marked by lines drawn with a toothpick dipped in a 1% aqueous solution of methylene blue. Under clean but not sterile conditions, surface skin abrasion was effected by a scapel blade scraping repeatedly within the blue line margins over the entire area. Examination of tissue slides prepared from biopsy specimens showed that the abrasion did relatively uniform damage to the epidermal layer of the rodent skin with most hair follicles unaffected. Oozing serous fluid was blotted with a cotton pad and the wounded area was swabbed again with the 10% polyvinylpyrrolidone-iodine solution. A piece of the thin insolubilized dextran sheet, 4 cm by 4 cm in size cut from the larger sheet just prepared, was positioned to cover the 3 cm by 3 cm wound in the centre of the transparent covering which was immediately secured by 3 strips of 0.7 cm wide elastic spandex polyurethane ribbons tied equidistantly apart from each other around the animal torso. When the thin insolubilized dextran sheet clung to the wound surface and sealed around its margin within 16 hours, the elastic ribbons were removed. All the animals were briefly immobilized to prevent them from interferring with the wound. The results are summarized in Table 1.

TABLE 1

WOUND HEALING AFTER SKIN INJURY BY ABRASION

| NO. OF RATS | COVERING | OBSERVATIONS |
| --- | --- | --- |
| | | CONTROLS |
| 5 | none | 3 rats formed thin eschar in 10 hr which separated from healed wound in 8-11 days; 2 rats wound infected, destroyed on day 5. |
| 5 | Impermeable plastic sheet from aerosol | 5 rats with serious fluid collected under sheet, no sign of healing when examined on day 7 |
| | | TEST |
| 15 | Thin insolubilized dextran sheet | 10 rats: no visible eschar, dextran sheet separated from healed tissue with hair in 4-7 days; immobilization failure - 3 rats chewed off covering; 1 rat wound infected; 1 killed by anesthetic. |

EXAMPLE 2

A hazy solution obtained by mixing 32 g of clinical grade dextran with a molecular weight of about 90,000 daltons, 132 ml of distilled water, 9 ml epichlorohydrin, and 12 ml of a 10 N sodium hydroxide solution according to the previously described procedure, was drained slowly in equal amounts into 4 polyethylene containers about 9 cm by 9 cm in their bottom area having in each a highly perforated thin cellophane sheet of same area. After 10 hr at 20° C., the coherent continuous insolubilized dextran sheets were removed from each container, washed thoroughly in hot water and placed all together in a large bath containing 30% glycerin in a 7% aqueous solution of polyvinylpyrrolidone-iodine complex. After 48 hours, the iodine complex diffused into the insolubilized dextran sheets which were removed and allowed to equilibrate with air moisture for at least 2 days before being packaged in thin polyethylene sheet pouches until use. The average thickness of the sheets thus prepared including the imbedded cellophane sheet was about 0.17 to 0.25 cm.

TEST 2

COVERING FOR WOUND DUE TO SKIN EXCISION

Dorsal skin wound, 3 cm across by 3.5 cm long was created by excision using curved Metsenbaum scissors on a total of 28 anaesthetized male Wistar rats weighing about 400±20 g each. Tissue slides prepared from biopsy specimens indicated that the injury affected mostly the middle dermal layer of skin destroying also the hair follicles with occasional damages to the panniculus carnosus muscle exposing the deep fascia. The uneven wound surface was cleansed with saline and approximately 4 cm by 4.5 cm insolubilized dextran sheets containing the antimicrobial polyvinylpyrrolidone iodine just prepared were positioned centrally over the wound on each of the 10 test animals. The plastic spandex ribbons used for holding the insolubilized dextran sheet coverings were removed next day when the coverings clung securely onto the wound surface. The other 18 animals served as controls with their wounds either exposed, covered with the plain insolubilized dextran sheets or with the impermeable but occlusive plastic sheet formed after discharging from an aerosol spray. All the rats were briefly immobilized to prevent scratching on the wounded area. The summary of results is given in Table 2.

TABLE 2

WOUND HEALING AFTER PARTIAL SKIN EXCISION

| NO. OF RATS | COVERING | OBSERVATIONS |
|---|---|---|
| | | CONTROLS |
| 8 | none | All formed eschar in 8–10 hr, 3 began draining on days 4–6 and destroyed; other healed after 25 ± 7 days with 65–100% skin contraction. |
| 5 | Impermeable plastic sheet from aerosol | Collected fluid under plastic sheet deteriorated, bacteria counts ~$10^6$/cm$^2$, tissue discoloration, no visible healing after 6–7 days. |
| 5 | Insolubilized dextran sheets no anti-microbials | 1 rat chewed off covering on day 6; 2 rats no fluid on wound, but bacterial count ~$10^4$/cm$^2$ on day 5, partial healing evident; 2 healed with 10–15% contraction on days 11–14. |
| | | TEST |
| 10 | Insolubilized dextran sheets impregnated with iodine complex | All healed in 10–14 days, 6 rats with partial and fragmentary covering separations starting on day 5, wound contraction 10–15%. |

EXAMPLE 3

The uniform insolubilized dextran paste was prepared from 43 g of clinical grade dextran (molecular weight: ~70,000 daltons), 284 ml of distilled water, 19 ml of a 10 N sodium hydroxide solution and 16 ml of epichlorohydrin in a 500-ml beaker according to the previously described procedure. After exhaustive washings with distilled water, and homogenization, the solid content of the free flowing thin paste was raised by evaporation to about 23% by weight. An amount of 1.25 g silver sulfadiazine was uniformly dispersed in 25 g of glycerin containing 0.8 g of U.S.P. Grade Mineral Oil, and added gradually in approximately equal portions into 100 g of the insolubilized dextran paste which was being kneaded mechanically in a small mixing bowl. The final composition of the milky paste was about 19% in insolubilized dextran solid, 20% glycerin, 0.6% USP mineral oil, and 1% silver sulfadiazine by weight. The medicated paste was transferred in 5 g portions into wide-mouthed plastic vials with caps.

TEST 3

BURN WOUNDS COVERED WITH INSOLUBILIZED DEXTRAN PASTE CONTAINING SILVER SULFADIAZINE

A total of 20 male Wistar rats (body weight: 400±20 g) was anaesthetized, and burned on their well-shaved dorsal skin once each for 10 seconds by a 2 cm-diameter stainless steel disc heated to 100° C according to a previous procedure (Wang, et al, Journal of Surgical Research, [1980], 28, 182). Examination of tissue slide prepared from biopsy specimens showed that the thermal injury caused full thickness skin damage at the area of contact. A solution containing $10^7$ bacteria/ml obtained from an infected rat skin wound in an earlier experiment was swabbed evenly two times over the stiff burned skin surface on all the animals. The burn wounds in a control group of 5 animals received no treatment. Another group of 5 control animals was escharectomized on the next day which also removed essentially the injured skin in full thickness exposing the fascia which was otherwise undisturbed. Insolubilized dextran paste with composition identical to the formulation given in EXAMPLE 3, but without the 1% silver sulfadiazine, was spread evenly thereon by a polyethylene stick to a thickness of about 0.1–0.15 cm, and the layer of covering was extended approximately 0.5 cm beyond the circumference of the wound onto the adjacent intact skin. The test group of 10 animals was also escharectomized, but the wounds were covered with an even 0.1–0.15 cm layer of the medicated paste. Bactierial counts of tissue under the eschar in both groups of escharectomized animals were about $10^3$–$10^5$ organissm/cm$^2$. The results are summarized in Table 3.

TABLE 3

BURN WOUND HEALING WITH SILVER SULFADIAZINE-INSOLUBILIZED DEXTRAN PASTE

| NO. OF RATS | COVERING | OBSERVATION |
|---|---|---|
| | | Controls |
| 5$^a$ | none | Erythema developed around eschar which cracked in 8–10 days, fluid drainage, eschar separation from healed wound in 20–47 days; 1 rat died in 5 days. |
| 5$^b$ | Insolubilized dextran paste, no silver sulfadiazine | Slight edema along wound edge, some tissue discoloration in 4 rats, wound almost closed by dermal cell migration 14–23 days, nearly complete healing 22–34 days; 1 rat chewed off covering. |
| | | Test |
| 10$^b$ | Insolubilized dextran paste with silver sulfadiazine | Some neighboring tissue edema, no fluid drainage; dermal cell layer migration visible in 5–7 days; almost complete healing in 14–24 days, 1 rat killed by anesthetic. |

$^a$no escharectomy
$^b$escharectomized

EXAMPLE 4

A solution prepared from 8 g of clinical grade dextran having an average molecular weight of 40,000 daltons, 30 ml of distilled water, and 6 ml of a 5 N sodium hydroxide solution was stirred vigorously without splashing in a 60 ml beaker while 2.5 ml of epichlorohydrin was added at once from a small graduated cylinder according to the previously described procedure. After washing with distilled water as described previously 10 ml of glycerin was mixed thoroughly with the loose paste, and the solid content of the insolubilized dextran was raised to about 21% by evaporation at room temperature with a stream of compressed air while the paste was being continuously kneaded. A volume of 5 ml of a thick brown aqueous solution containing 15% by weight of polyvinylpyrrolidone-iodine complex and some petrolatum were then mixed thoroughly with the paste to give a final composition of about 18% solid content of the insolubilized dextran, 20% glycerin, 0.6% petrolatum, 2% poly-vinylpyrrolidone-iodine complex. The paste was then pressed into thin sheets of 0.1 cm in thickness as described.

TEST 4

REDUCTION OF EVAPORATIVE LOSS FROM SKIN WOUND WITH INSOLUBILIZED DEXTRAN PASTE COVERING

A similar procedure as described in TEST 2 was used to inflict a circular partial thickness skin wound, 2 cm in diameter, on the back of each of the 12 anaesthetized male Wistar rats weighing 400±20 g. The control group of 4 animals had their circular wound covered with the impermeable plastic sheet derived from an aerosol spray. A 1-ml syringe with a fine hypodermic needle was used to puncture the occlusive impermeable plastic covering and withdraw the serous fluid collected thereunder at regular intervals. For the first hour, 0.1 ml per ½ hr was collected. Thereafter, the fluid oozing reduced to 0.03 ml for the next 3 hr. (see Table 4). If not absorbed, the fluid could remain under the occlusive plastic covering for many days (see also Table 1, second group of Controls), and cause delay in wound healing. However, without any covering, the partial thickness circular wounds were found by hygrometric measurements (see Wang et al. Journal Surgical Research, [1980], 28, 182) to undergo almost twice the evaporative loss even after 5 days as compared to a similar wound with the insolubilized dextran covering after only 4 hours (30 mg $H_2O$/hr/$cm^2$ with no covering versus 17 mg $H_2O$/hr/$cm^2$, see Table 4). The summary of results is given in the following table:

TABLE 4
WOUND EVAPORATIVE LOSS REDUCTION BY INSOLUBILIZED DEXTRAN SHEET MADE FROM THE PASTE

| NO. OF RATS | COVERING | OBSERVATIONS |
| --- | --- | --- |
| | | CONTROLS |
| 5 | Impermeable plastic sheet from aerosol | Total volume of serious fluid collected: 1st day - 0.23 ml; 2nd day - 0.1 ml; 3rd day - 0.04 ml; if collected at once on 4th day - 0.4 ml. |
| 5 | none | Evaporative loss: 1st hr - 91 mg $H_2O$/hr/$cm^2$; eschar formed, 2nd day - 56 mg $H_2O$/hr/$cm^2$ |
| | | Test |
| 5 | Insolubilized dextran sheet from paste with iodine complex | Covering external surface tack-free in 4 hr - evaporative loss 17 mg $H_2O$/hr/$cm^2$; 2nd day - 10 mg $H_2O$/hr/$cm^2$; 5th day - 4 mg $H_2O$/hr/$cm^2$; no fluid collected in any wound. |

EXAMPLE 5

An amount of 40 ml of a 10 N solution of potassium hydroxide was added to 220 ml of double-distilled water. Seventy grams of dextran C powder having an average molecular weight of 80,000 daltons was added in portions into the alkaline solution with stirring. A graduated cylinder was used to measure 28 ml of epichlorohydrin which was added at once to the alkaline dextran solution. The vigorous stirring was continued until the yellow hazy solution almost turned clear. A polyethylene tray 21 cm×32 cm by 3 cm high was layered at the bottom with a piece of highly perforated cellophane sheet of about the same area. A volume of 134 ml of the already stirred alkaline dispersion just prepared was drained along a 1-cm diameter glass rod into the platic tray which was then covered with a lid and left undisturbed for 10 hr at 25° C. The remaining about 85 ml of the alkaline dispersion was drained similarly into a 14 cm×21 cm by 3 cm high polyethylene tray also layered with a sheet of cellophane as before, and the tray was covered and left undisturbed for 8 hr. at 30° C. The insolubilized dextran sheets were removed from the trays and placed in running hot water for 24 hr. as previously described. At the end of this period, the smooth continuous sheets showed no visible dimension expansion or warping. If loosely-woven textile materials were used in place of the highly perforated cellophane sheets, severe warping and dimension distortion will occur causing damage to the otherwise smooth continuous sheet essentially free of any pinhole imperfections. The washed sheets were then transferred into a large bath containing 40% glycerin in distilled water and 20% polyvinylpyrrolidone-iodine complex by weight. After 48 hr. the dark brown sheets were allowed to equilibrate with air moisture for 48 hr. which reduced the thickness of the sheets to 0.15–0.2 cm. The sheets may be cut to smaller sizes for package in polyethylene sheet bags and heat-sealed.

EXAMPLE 6

A volume of 200 ml of distilled water was added to 315 ml of 2 N lithium hydroxide, and 110 g dextran was then dissolved therein to afford a light yellow solution. Epichlorohydrin in the amount of 27 g was added into the well-stirred alkaline solution as previously described. The hazy alkaline dispersion was drained into a 43 cm×43 cm by 4 cm high tray layered with a piece of cellophane sheet to cover the entire bottom. The tray and its contents were covered and left undisturbed at 19° C. for 12 hr. The insolubilized dextran sheet was then removed, washed, impregnated with a 4% polyvinylpyrrolidone-iodine complex solution in 20% isopropyl alcohol in propylene glycol containing 0.9% castor oil and packaged.

EXAMPLE 7

A uniform paste was obtained using 216 g dextran C, 1420 ml distilled water, 97 ml of 10 N sodium hydroxide and 80 ml epichlorohydrin as previously described and as in Example 3. The solid content of the paste was adjusted to 21% of a weight to weight basis, and the stock paste may be divided into several lots for further addition of humectants, antimicrobial agent or pressed into sheets of various sizes and packaged as described in Examples 3 or 4.

Tests carried out with the coherent continuous insolubilized dextran sheets and pastes of which Examples 5 to 7 are exemplary have established results comparable to those set out in Tests described above.

It will be understood that the above examples are illustrative only and the invention is not limited thereto.

I claim:

1. A wound covering material comprising epichlorohydrin insolubilized dextran C polysaccharide sheet impregnated with a humectant for application to skin wound for covering and protection thereof.

2. The wound covering material of claim 1 wherein the humectant comprises glycerin and/or propylene glycol.

3. The wound covering material of claim 2 having a stabilizing sheet of water swellable polymer material embedded therein.

4. The wound covering material of claim 1 having an effective antimicrobial compound consisting of silver sulfadiazine or polyvinylpyrrolidone-iodine complex.

5. The wound covering material comprising an epichlorohydrin insolubilized dextran paste pressed into sheets, said sheets containing glycerin and/or propylene glycol as humectant, and further containing a medicament selected from silver sulfadiazine and polyvinylpyrrolidone-iodine complex.

* * * * *